US011185576B2

(12) United States Patent
Seyedin et al.

(10) Patent No.: US 11,185,576 B2
(45) Date of Patent: *Nov. 30, 2021

(54) FLEXIBLE TISSUE MATRIX AND METHODS FOR JOINT REPAIR

(71) Applicant: Isto Technologies II, LLC, Hopkinton, MA (US)

(72) Inventors: Mitchell S. Seyedin, St. Louis, MO (US); Anthony J. Ward, St. Louis, MO (US); Matthew Matava, Chesterfield, MO (US)

(73) Assignee: Isto Technologies II, LLC, Chicago, IL (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/353,004

(22) Filed: Mar. 14, 2019

(65) Prior Publication Data

US 2019/0209666 A1    Jul. 11, 2019

Related U.S. Application Data

(63) Continuation of application No. 13/837,849, filed on Mar. 15, 2013, now Pat. No. 10,245,306.

(60) Provisional application No. 61/727,454, filed on Nov. 16, 2012.

(51) Int. Cl.
| | |
|---|---|
| *A61K 35/28* | (2015.01) |
| *A61L 27/26* | (2006.01) |
| *A61L 27/56* | (2006.01) |
| *A61K 38/51* | (2006.01) |
| *A61K 38/18* | (2006.01) |
| *A61K 38/19* | (2006.01) |
| *A61K 38/20* | (2006.01) |
| *A61K 38/30* | (2006.01) |
| *A61K 38/39* | (2006.01) |
| *A61L 27/52* | (2006.01) |
| *A61L 27/58* | (2006.01) |
| *A61K 38/48* | (2006.01) |

(52) U.S. Cl.
CPC ............. *A61K 38/51* (2013.01); *A61K 38/18* (2013.01); *A61K 38/1825* (2013.01); *A61K 38/1841* (2013.01); *A61K 38/1858* (2013.01); *A61K 38/1875* (2013.01); *A61K 38/193* (2013.01); *A61K 38/20* (2013.01); *A61K 38/30* (2013.01); *A61K 38/39* (2013.01); *A61K 38/4886* (2013.01); *A61L 27/26* (2013.01); *A61L 27/52* (2013.01); *A61L 27/56* (2013.01); *A61L 27/58* (2013.01)

(58) Field of Classification Search
CPC combination set(s) only.
See application file for complete search history.

(56) References Cited

U.S. PATENT DOCUMENTS

| | | |
|---|---|---|
| 4,438,102 A | 3/1984 | Ganci |
| 4,440,680 A | 4/1984 | Cioca |
| 4,692,371 A | 9/1987 | Morman et al. |
| 4,789,663 A | 12/1988 | Wallace et al. |
| 4,818,633 A | 4/1989 | Dinwoodie et al. |
| 4,846,835 A | 7/1989 | Grande |
| 4,904,259 A | 2/1990 | Itay |
| 4,957,744 A | 9/1990 | della Valle et al. |
| 5,053,050 A | 10/1991 | Itay |
| 5,139,527 A | 8/1992 | Redl et al. |
| 5,206,023 A | 4/1993 | Hunziker |
| 5,290,552 A | 3/1994 | Sierra et al. |
| 5,368,858 A | 11/1994 | Hunziker |
| 5,475,052 A | 12/1995 | Rhee et al. |
| 5,565,519 A | 10/1996 | Rhee et al. |
| 5,597,897 A | 1/1997 | Ron et al. |
| 5,644,049 A | 7/1997 | Giusti et al. |
| 5,700,289 A | 12/1997 | Breitbart et al. |
| 5,723,508 A | 3/1998 | Healy et al. |
| 5,736,372 A | 4/1998 | Vacanti et al. |
| 5,769,899 A | 6/1998 | Schwartz et al. |
| 5,842,477 A | 12/1998 | Naughton et al. |
| 5,853,746 A | 12/1998 | Hunziker |
| 5,855,608 A | 1/1999 | Brekke et al. |
| 5,891,455 A | 4/1999 | Sittinger et al. |
| 5,916,585 A | 6/1999 | Cook et al. |
| 5,972,385 A | 10/1999 | Liu et al. |

(Continued)

FOREIGN PATENT DOCUMENTS

| | | |
|---|---|---|
| CA | 2261292 C | 9/2008 |
| CA | 2445356 C | 2/2010 |

(Continued)

OTHER PUBLICATIONS

International Search Report and Written Opinion relating to International Application No. PCT/US07/70631, dated Sep. 16, 2008, 10 pgs.

International Search Report and Written Opinion relating to International Application No. PCT/US2006/046576, dated Oct. 22, 2008, 8 pgs.

International Search Report and Written Opinion relating to International Application No. PCT/US2013/070573, dated Mar. 19, 2014, 9 pgs.

(Continued)

*Primary Examiner* — Arthur S Leonard
(74) *Attorney, Agent, or Firm* — Polsinelli PC

(57) ABSTRACT

A synthetic, flexible tissue matrix and methods for repairing hyaline cartilage defects in a joint using the flexible tissue matrix are described. The flexible tissue matrix includes a high molecular weight polycaprolactone polymer entangled with a polysaccharide such as hyaluronic acid. In the methods, autologous bone mesenchymal stem cells are introduced to a joint by a microfracturing technique, and a membrane made of the flexible matrix is applied to the joint. Cartilage which forms in the joint is hyaline cartilage rather than fibrocartilage.

30 Claims, No Drawings

(56) References Cited

U.S. PATENT DOCUMENTS

| | | | |
|---|---|---|---|
| 6,051,701 A | 4/2000 | Cialdi et al. |
| 6,060,053 A | 5/2000 | Atala |
| 6,193,991 B1 | 2/2001 | Shukla |
| 6,224,893 B1 | 5/2001 | Langer et al. |
| 6,281,256 B1 | 8/2001 | Harris et al. |
| 6,303,585 B1 | 10/2001 | Spiro et al. |
| 6,328,765 B1 | 12/2001 | Hardwick et al. |
| 6,339,074 B1 | 1/2002 | Cialdi et al. |
| 6,344,488 B1 | 2/2002 | Chenite et al. |
| 6,355,699 B1 | 3/2002 | Vyakarnam et al. |
| 6,378,527 B1 | 4/2002 | Hungerford et al. |
| 6,395,253 B2 | 5/2002 | Levy et al. |
| 6,454,811 B1 | 9/2002 | Sherwood et al. |
| 6,514,522 B2 | 2/2003 | Domb |
| 6,534,084 B1 | 3/2003 | Vyakarnam et al. |
| 6,579,978 B1 | 6/2003 | Renier et al. |
| 6,596,274 B1 | 7/2003 | Abatangelo et al. |
| 6,626,950 B2 | 9/2003 | Brown et al. |
| 6,637,437 B1 | 10/2003 | Hungerford et al. |
| 6,662,805 B2 | 12/2003 | Frondoza et al. |
| 6,673,285 B2 | 1/2004 | Ma |
| 6,689,747 B2 | 2/2004 | Filvaroff et al. |
| 6,696,073 B2 | 2/2004 | Boyce et al. |
| 6,737,072 B1 | 5/2004 | Angele et al. |
| 6,852,330 B2 | 2/2005 | Bowman et al. |
| 6,886,568 B2 | 5/2005 | Frondoza et al. |
| 6,949,252 B2 | 9/2005 | Mizuno et al. |
| 7,087,745 B1 | 8/2006 | Pallado et al. |
| RE39,321 E | 10/2006 | MacPhee et al. |
| 7,316,822 B2 | 1/2008 | Binette et al. |
| 7,375,077 B2 | 5/2008 | Mao |
| 7,446,131 B1 | 11/2008 | Liu et al. |
| 7,824,711 B2 | 11/2010 | Kizer et al. |
| 8,192,759 B2 | 6/2012 | Seyedin et al. |
| 8,444,968 B2 | 5/2013 | Seyedin et al. |
| 8,512,730 B2 | 8/2013 | Seyedin et al. |
| 8,580,289 B2 | 11/2013 | Seyedin et al. |
| 2002/0004225 A1 | 1/2002 | Hart et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0062151 A1 | 5/2002 | Altman et al. |
| 2002/0064559 A1 | 5/2002 | Lee et al. |
| 2002/0123142 A1 | 9/2002 | Hungerford et al. |
| 2002/0133235 A1 | 9/2002 | Hungerford et al. |
| 2002/0183858 A1 | 12/2002 | Contiliano et al. |
| 2003/0039695 A1 | 2/2003 | Geistlich et al. |
| 2003/0040113 A1 | 2/2003 | Mizuno et al. |
| 2003/0099620 A1 | 5/2003 | Zaleske et al. |
| 2004/0001879 A1 | 1/2004 | Guo et al. |
| 2004/0033212 A1 | 2/2004 | Thomson et al. |
| 2004/0048796 A1 | 3/2004 | Hariri et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0117033 A1 | 6/2004 | Frondoza et al. |
| 2004/0126405 A1 | 7/2004 | Sahatjian et al. |
| 2004/0134502 A1 | 7/2004 | Mizuno et al. |
| 2004/0138664 A1 | 7/2004 | Bowman |
| 2004/0151705 A1 | 8/2004 | Mizuno et al. |
| 2004/0181240 A1 | 9/2004 | Tseng et al. |
| 2004/0191900 A1 | 9/2004 | Mizuno et al. |
| 2004/0219182 A1 | 11/2004 | Gomes et al. |
| 2004/0228901 A1 | 11/2004 | Trieu et al. |
| 2005/0038520 A1 | 2/2005 | Binette et al. |
| 2005/0043814 A1 | 2/2005 | Kusanagi et al. |
| 2005/0064042 A1 | 3/2005 | Vunjak-Novakovic et al. |
| 2005/0079202 A1 | 4/2005 | Chen et al. |
| 2005/0113937 A1 | 5/2005 | Binette et al. |
| 2005/0142163 A1 | 6/2005 | Hunter et al. |
| 2005/0152882 A1 | 7/2005 | Kizer et al. |
| 2005/0152949 A1 | 7/2005 | Hotchkiss et al. |
| 2005/0177249 A1 | 8/2005 | Kladakis et al. |
| 2005/0186283 A1 | 8/2005 | Geistlich et al. |
| 2005/0186673 A1 | 8/2005 | Geistlich et al. |
| 2005/0196460 A1 | 9/2005 | Malinin |
| 2005/0222687 A1 | 10/2005 | Vunjak-Novakovic et al. |
| 2005/0226856 A1 | 10/2005 | Ahlfors |
| 2005/0251268 A1 | 11/2005 | Truncale |
| 2005/0288796 A1 | 12/2005 | Awad et al. |
| 2006/0002979 A1 | 1/2006 | Ashammakhi et al. |
| 2006/0008530 A1 | 1/2006 | Seyedin et al. |
| 2006/0019389 A1 | 1/2006 | Yayon et al. |
| 2006/0024377 A1 | 2/2006 | Ying et al. |
| 2006/0024826 A1 | 2/2006 | Bonassar et al. |
| 2006/0029679 A1 | 2/2006 | Dolecek |
| 2006/0111778 A1 | 5/2006 | Michalow |
| 2006/0128016 A1 | 6/2006 | Tokushima et al. |
| 2006/0140988 A1 | 6/2006 | Chen et al. |
| 2006/0147547 A1 | 7/2006 | Yayon |
| 2006/0153815 A1 | 7/2006 | Seyda et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0251631 A1 | 11/2006 | Adkisson, IV et al. |
| 2007/0014867 A1 | 1/2007 | Kusanagi et al. |
| 2007/0031471 A1 | 2/2007 | Peyman |
| 2007/0038299 A1 | 2/2007 | Stone et al. |
| 2007/0041952 A1 | 2/2007 | Guilak et al. |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2008/0009942 A1 | 1/2008 | Mizuno et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0097605 A1 | 4/2008 | Pastorello et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0274157 A1 | 11/2008 | Vunjak-Novakovic et al. |
| 2008/0300322 A1* | 12/2008 | Shukla ............... A61K 47/44 514/782 |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale et al. |
| 2010/0086594 A1 | 4/2010 | Amit et al. |
| 2010/0168856 A1 | 7/2010 | Long et al. |
| 2011/0009963 A1 | 1/2011 | Binnette et al. |
| 2011/0052705 A1 | 3/2011 | Malinin |
| 2011/0070271 A1 | 3/2011 | Truncate et al. |
| 2011/0086081 A1 | 4/2011 | To et al. |
| 2011/0091517 A1 | 4/2011 | Binette et al. |
| 2011/0097381 A1 | 4/2011 | Binette et al. |
| 2011/0196508 A1 | 8/2011 | Truncale et al. |
| 2011/0256095 A1 | 10/2011 | Seyedin et al. |
| 2012/0156265 A1 | 6/2012 | Binette et al. |
| 2016/0101213 A1 | 4/2016 | Seyedin et al. |

FOREIGN PATENT DOCUMENTS

| | | |
|---|---|---|
| CA | 2445558 C | 2/2010 |
| CA | 2475905 C | 4/2010 |
| CA | 2522133 C | 11/2010 |
| CA | 2496184 C | 4/2012 |
| CA | 2563082 C | 7/2012 |
| CA | 2441994 C | 8/2012 |
| CA | 2487029 C | 8/2012 |
| EP | 0610423 B1 | 5/1997 |
| EP | 1538196 A1 | 6/2005 |
| EP | 1561481 A2 | 8/2005 |
| EP | 1410811 B1 | 10/2008 |
| GB | 2175507 A | 12/1986 |
| WO | 85/05274 A1 | 12/1985 |
| WO | 90/00060 A1 | 1/1990 |

(56) References Cited

FOREIGN PATENT DOCUMENTS

| | | |
|---|---|---|
| WO | 93/00050 A1 | 1/1993 |
| WO | 93/11803 A1 | 6/1993 |
| WO | 94/01468 A1 | 1/1994 |
| WO | 95/31157 A1 | 11/1995 |
| WO | 96/28539 A1 | 9/1996 |
| WO | 96/37165 A1 | 11/1996 |
| WO | 98/04681 A2 | 2/1998 |
| WO | 00/55300 A1 | 9/2000 |
| WO | 01/01895 A1 | 1/2001 |
| WO | 01/35968 A1 | 5/2001 |
| WO | 02/72662 A1 | 9/2002 |
| WO | 02/076335 A2 | 10/2002 |
| WO | 03/039615 A2 | 5/2003 |
| WO | 03/077794 A2 | 9/2003 |
| WO | 2004/028584 A1 | 4/2004 |
| WO | 2005/060987 A1 | 7/2005 |
| WO | 2005/061018 A1 | 7/2005 |
| WO | 2006/033698 A2 | 3/2006 |
| WO | 2006/058221 A2 | 6/2006 |
| WO | 2006/068972 A2 | 6/2006 |
| WO | 2006/071694 A1 | 7/2006 |
| WO | 2006/113642 A1 | 10/2006 |
| WO | 2007/067637 A2 | 6/2007 |
| WO | 2007/102149 A2 | 9/2007 |
| WO | 2007/143726 A2 | 12/2007 |
| WO | 2009/108934 A2 | 9/2009 |
| WO | 2014/078792 A1 | 5/2014 |

OTHER PUBLICATIONS

Jalil et al., "Biodegradable poly(lactic acid) and poly(lactide-co-glycolide) microcapsules: problems associated with preparative techniques and release properties", J. Microencapsulation, 1990, pp. 297-325, vol. 7, No. 3.
Jeong et al., "Three-dimensional polycaprolactone scaffold-conjugated bone morphogenetic protein-2 promotes cartilage regeneration from primary chondrocytes in vitro and in vivo without accelerated endochondral ossification", Journal of Biomedical Materials Research Part A, 2012, pp. 2088-2096, vol. 100A, No. 8.
Jin et al., "Human Amniotic Membrane as a Delivery Matrix for Articular Cartilage Repair", Tissue Engineering, 2007, pp. 693-703, vol. 13, No. 4.
Kon et al., "Second Generation Issues in Cartilage Repair", Sports Med Arthrosc Rev, 2008, pp. 221-229, vol. 16, No. 4.
Kuettner, "Biochemistry of Articular Cartilage in Health and Disease", Clinical Biochemistry, 1992, pp. 155-163, vol. 25.
Kuo et al., "Chemical Modification of Hyaluronic Acid by Carbodiimides", Bioconjugate Chem, 1991, pp. 232-241, vol. 2, No. 4.
Kurzweil et al., "New Therapeutic Options for Managing the Arthritic Knee", A Supplement to the American Journal of Orthopedics, Feb. 2004, pp. 35-39, vol. 33, Supp. 2.
Libera et al., Cartilage Engineering, Fundamentals of Tissue Engineering and Regenerative Medicine, 2009, Chapter 18, Springer-Verlag, Berlin Heidelberg, pp. 233-242.
Marmotti et al., "One-step osteochondral repair with cartilage fragments in a composite scaffold", Knee Surg Sports Traumatol Arthrosc, 2012, 12 pgs.
Mason et al., "Attachment of hyaluronic acid to polypropylene, polystyrene, and polytetrafluoroethylene", Biomaterials, 2000, pp. 31-36, vol. 21.
Minas et al., "Current Concepts in the Treatment of Articular Cartilage Defects", Orthopedics, 1997, pp. 525-538, vol. 20, No. 6.
Nehrer et al., "Three-year clinical outcome after chondrocyte transplantation using a hyaluronan matrix for cartilage repair", European Journal of Radiology, 2006, pp. 3-8, vol. 57.
Obradovic et al., "Integration of engineered cartilage", Journal of Orthopaedic Research, 2001, pp. 1089-1097, vol. 19, No. 6.
Oh et al., "In vitro and in vivo characteristics of PCL scaffolds with pore size gradient fabricated by a centrifugation method", Biomaterials, 2007, pp. 1664-1671, vol. 28.
Peretti et al., "Bonding of Cartilage Matrices with Cultured Chondrocytes: An Experimental Model", Journal of Orthopaedic Research, 1998, pp. 89-95, vol. 16, No. 1.
Peretti et al., "Cell-Based Tissue-Engineered Allogeneic Implant for Cartilage Repair", Tissue Engineering, 2000, pp. 567-576, vol. 6, No. 5.
Peretti et al., "A Biomechanical Analysis of an Engineered Cell-Scaffold Implant for Cartilage Repair", Annals of Plastic Surgery, 2001, pp. 533-537, vol. 46, No. 5.
Peretti et al., "In vitro bonding of pre-seeded chondrocytes", Sport Sci Health, 2007, pp. 29-33, vol. 2.
Robinson et al., "Regenerating Hyaline Cartilage in Articular Defects of Old Chickens Using Implants of Embryonal Chick Chondrocytes Embedded in a New Natural Delivery Substance", Calcified Tissue International, 1990, pp. 246-253, vol. 46.
Sampath et al., "In vitro transformation of mesenchymal cells derived from embryonic muscle into cartilage in response to extracellular matrix components of bone", PNAS, 1984, pp. 3419-3423.
Schreiber et al., "A Method for Tissue Engineering of Cartilage by Cell Seeding on Bioresorbable Scaffolds", Annals New York Academy of Sciences, 1999, pp. 398-404, vol. 875.
Schwarz et al., "The Influence of Fibrin Sealant on Demineralized Bone Matrix-Dependent Osteoinduction", Clinical Orthopaedics and Related Research, 1989, pp. 282-287, No. 238.
Seliktar, "Nature's Healing Matrix", Lecture Bulletin, Technion Focus, May 2006, 1 page.
Sierra et al., "Fibrin-Collagen Adhesive Drug Delivery System for Tumor Therapy", The 19th Annual Meeting of the Society for Biomaterials, Apr. 28-May 2, 1993, p. 257, vol. 16.
Stone et al., "New Techniques For Cartilage Repair and Replacement", Knee Ligament Rehabilitation, Ellenbecker T.S., Jun. 2000, 11 pages.
Uematsu et al., "Cartilage regeneration using mesenchymal stem cells and a three-dimensional poly-lactic-glycolic acid (PLGA) scaffold", Biomaterials, 2005, pp. 4273-4279, vol. 26, No. 20.
Wakitani et al., "Repair of Rabbit Articular Surfaces With Allograft Chondrocytes Embedded in Collagen Gel", The Journal of Bone and Joint Surgery, 1989, pp. 74-80, vol. 71-B, No. 1.
Wang et al., "Morphological development in absorbable poly(glycolide), poly(glycolide-co-lactide), and poly(glycolide-co-caprolactone) copolymers during isothermal crystallization", Polymer, 2000, pp. 621-628, vol. 41.
Zhao et al., "Synthesis and characterization of a novel double crosslinked hyaluronan hydrogel", Journal of Materials Science: Materials in Medicine, 2002, pp. 11-16, vol. 13.
Armentano et al., "Biodegradable polymer matrix nanocomposites for tissue engineering: A review", Polymer Degradation and Stability, 2010, pp. 2126-2146, vol. 95.
Cha et al., "The biodegradability of polyester blends", Biomaterials, 1990, pp. 108-112, vol. 11.
Ciardelli et al., "Blends of Poly-(e-caprolactone) and Polysaccharides in Tissue Engineering Applications", Biomacromolecules, 2005, pp. 1961-1976, vol. 6, No. 4.
Helmsworth et al., "Molecular Surgery of the Basement Membrane by the Argon Laser", Lasers in Surgery and Medicine, 1990, pp. 576-583, vol. 10, No. 6.
Hurst et al., "Rehabilitation Following Microfracture for Chondral Injury in the Knee", Clin Sports Med., 2010, pp. 257-265, vol. 29, No. 2.
Kim et al., "Synthesis and Characterization of Injectable Poly(N-isopropylacrylamide-co-acrylic acid) Hydrogels with Proteolytically Degradable Cross-Links", Biomacromolecules, 2003, pp. 1214-1223, vol. 4, No. 5.
Kranz et al., "Physicomechanical Properties of Biodegradable Poly(D,L-lactide) and Poly(D,L-lactide-co-glycolide) Films in the Dry and Wet States", Journal of Pharmaceutical Sciences, 2000, pp. 1558-1566, vol. 89, No. 12.
Sannino et al., "Biodegradable Cellulose-based Hydrogels: Design and Applications", Materials, 2009, pp. 353-373, vol. 2.
Sarasam et al., "Blending Chitosan with Polycaprolactone: Porous Scaffolds and Toxicity", Macromolecular Bioscience, 2007, pp. 1160-1167, vol. 7.

(56) References Cited

OTHER PUBLICATIONS

Schagemann et al., "The effect of scaffold composition on the early structural characteristics of chondrocytes and expression of adhesion molecules", Biomaterials, 2010, pp. 2798-2805, vol. 31.

Steadman et al., "Microfracture: Surgical Technique and Rehabilitation to Treat Chondral Defects", Clinical Orthopaedics and Related Research, 2001, pp. S362-S369, No. 391S.

Steadman et al., "Microfracture to Treat Full-Thickness Chondral Defects: Surgical Technique, Rehabilitation, and Outcomes", The Journal of Knee Surgery, 2002, pp. 170-176, vol. 15, No. 3.

UCLA, Department of Chemistry, Extraction (Part 1), Dec. 30, 2013; 6 pgs., http://www.chem.ucla.edu/bacher/Specialtopics/extraction.html.

Vangsness et al., "Restoring Articular Cartilage in the Knee", A Supplement to the American Journal of Orthopedics, 2004, pp. 29-39, vol. 33, No. 2 Suppl.

Zhang et al., "Preparation of Hydroxyapatite / Poly(e-caprolactone) Hybrid Microspheres for Drug Release System", Key Engineering Materials, 2007, pp. 1045-1048, vols. 330-332.

Amiel et al., "Rib Perichondrial Gralls for the Repair of Full-Thickness Articular-Cartilage Defects", The Journal of Bone and Joint Surgery, 1985, pp. 911-920, vol. 67A.

Benesova et al., "Stability Evaluation of n-Alkyl Hyaluronic Acid Derivates by DSC and TG Measurement", Journal of Thermal Analysis and Calorimetry, 2006, pp. 341-348, vol. 83, No. 2.

Benjamin et al., "Biology of Fibrocartilage Cells", International Review of Cytology, 2004, pp. 1-45, vol. 233.

Blein-Sella et al., "Rabbit Articular Chondrocyte Functional Toxicity Test", Methods in Molecular Biology, 1995, Chapter 19, pp. 169-175, vol. 43.

Cheng et al., "Chondrogenic Differentiation of Adipose-Derived Adult Stem Cells by a Porous Scaffold Derived from Native Articular Cartilage Extracellular Matrix", Tissue Engineering: Part A, 2009, pp. 231-241, vol. 15, No. 2.

De Gennes, "Reptation of a Polymer Chain in the Presence of Fixed Obstacles", The Journal of Chemical Physics, 1971, pp. 572-579, vol. 55, No. 2.

Dietz et al., "Alterations of Collagen mRNA Expression During Retinoic Acid Induced Chondrocyte Modulation: Absence of Untranslated α1(I) mRNA in Hyaline Chondrocytes", Journal of Cellular Biochemistry, 1993, pp. 57-68, vol. 52.

Edwards, "The statistical mechanics of polymerized material", Proc. Phys. Soc., 1967, pp. 9-16, vol. 92.

Ekaputra et al., "The three-dimensional vascularization of growth factor-releasing hybrid scaffold of poly (ε-caprolactone)/collagen fibers and hyaluronic acid hydrogel", Biomaterials, 2011, pp. 8108-8117, vol. 32.

European Search Report from related European Application No. 06839104.4, dated Oct. 28, 2009, 6 pgs.

European Search Report from related European Application No. 13855076.9, dated Aug. 11, 2016, 9 pgs.

European Search Report from related European Application No. 05812025.4, dated Jul. 29, 2011, 6 pgs.

Fu et al., "Autologous Chondrocyte Implantation Versus Debridement for Treatment of Full-Thickness Chondral Defects of the Knee—An Observational Cohort Study With 3-Year Follow-up", The American Journal of Sports Medicine, 2005, pp. 1658-1666, vol. 33, No. 11.

Fukuzaki et al., "In vivo characteristics of low molecular weight copolymers composed of L-lactic acid and various DL-hydroxy acids as biodegradable carriers for drug delivery systems", Biomaterials, 1990, pp. 441-446, vol. 11.

Gilbert, "Current Treatment Options for the Restoration of Articular Cartilage", The American Journal of Knee Surgery, 1998, pp. 42-46, vol. 11, No. 1.

Gombotz et al., "Biodegradable Polymers for Protein and Peptide Drug Delivery", Bioconjugate Chem., 1995, pp. 332-351, vol. 6, No. 4.

Gross, "Cartilage Resurfacing—Filling Defects", The Journal of Arthroplasty, 2003, pp. 14-17, vol. 18, No. 3.

Hollinger, "Preliminary report on the osteogenic potential of a biodegradable copolymer of polyactide (PLA) and polyglycolide (PGA)", Journal of Biomedical Materials Research, 1983, pp. 71-82, vol. 17.

Hunziker, "Articular cartilage repair: basic science and clinical progress. A review of the current status and prospects", Osteoarthritis and Cartilage, 2001, pp. 432-463, vol. 10, No. 6.

"Hyaluronan-Modified Surfaces for Medical Devices", www.devicelink.com/grabber.php3?URL=http://www.devicelink.com/mddi/archive., Medical Device & Diagnostic Industry Magazine, 1999, print date Oct. 14, 2005, 15 pgs.

\* cited by examiner

FLEXIBLE TISSUE MATRIX AND METHODS FOR JOINT REPAIR

CROSS-REFERENCE TO RELATED APPLICATIONS

This application is a Continuation of U.S. application Ser. No. 13/837,849, filed Mar. 15, 2013, which claims priority to U.S. Provisional Application No. 61/727,454, filed Nov. 16, 2012, entitled "FLEXIBLE TISSUE MATRIX", the entire disclosures of which are hereby incorporated by reference.

TECHNICAL FIELD

The present disclosure relates generally to a synthetic, flexible tissue matrix and methods for repairing hyaline cartilage defects in a joint using the flexible tissue matrix as described.

BACKGROUND

Defects of articular joints are significant sources of pain, discomfort and disability. These defects, such as full-thickness chondral defects, may be associated with osteoarthritis or other disease, traumatic injury and/or age or use-related degeneration of articular cartilage. Morbidity associated with defects of hyaline cartilage comprised by articular joints is responsible for significant economic, health and social costs.

Current treatments for repair or amelioration of joint problems include microfracture, abrasion and drilling. These interventions involve exposing a joint containing a defect to mesenchymal stem cells. As a result of such interventions, the mesenchymal stem cells may infiltrate the defect, and differentiate into fibrocartilage over time. However, fibrocartilage has a structure and molecular composition distinct from that of the hyaline cartilage found in joints. Fibrocartilage generally provides only short-term improvement, typically lasting less than two years. Alternative treatments are, therefore, needed.

BRIEF SUMMARY OF THE INVENTION

In one aspect, the present disclosure provides a tissue matrix for supporting repair of biological tissues comprising a high molecular weight caprolactone polymer entangled with a polysaccharide. The high molecular weight caprolactone polymer may be selected from polycaprolactone; a co-polymer of polylactic acid and polycaprolactone; a co-polymer of polyglycolic acid and polycaprolactone; a co-polymer of polylactic acid, polyglycolic acid and polycaprolactone; a co-polymer of polyethylene glycol, polylactic acid and polycaprolactone; a co-polymer of polyethylene glycol, polyglycolic acid and polycaprolactone; and a co-polymer of polyethylene glycol, polylactic acid, polyglycolic acid and polycaprolactone A tissue matrix may further include at least one flexibility agent. The flexibility agent may be selected from triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate, and any combination thereof. Alternatively, the flexibility agent may be selected from polyethylene glycol, polyethylene glycol monoalkyl ether, propylene glycol, glycerin, triacetin, and any combination thereof. In a tissue matrix, the polysaccharide may comprise hyaluronic acid polymers. A tissue matrix may further include at least one growth factor which may be for example a bone morphogenetic protein. A growth factor may be an isolated growth factor previously isolated from allogenic bone. A growth factor may be selected from basic fibroblast growth factor (bFGF), transforming growth factor (TGF-β), BMP-2, ADMP-1, a hedgehog protein, an insulin-like growth factor, a platelet-derived growth factor, an interleukin, a colony-stimulating factor, and an activin. A tissue matrix may further include a type I collagen or a type II collagen. A tissue matrix may be combined at a defect site in a joint with a DBM composition, crushed bone, or allogenic bone. A tissue matrix may be formed as a membrane, such as for example a membrane having a thickness of at least about 0.5 mm up to about 3 mm.

In another aspect, the present disclosure provides a method for repairing a hyaline cartilage defect in a joint in a mammal, the method comprising: infiltrating the joint with autologous mesenchymal stem cells; and applying to the joint a membrane comprising any tissue matrix as described in the foregoing which comprises a high molecular weight caprolactone polymer entangled with a polysaccharide. Infiltrating the joint with autologous mesenchymal stem cells may involve, for example, introducing at least one aperture into the bone underlying the joint, wherein the at least one aperture is sufficiently large to allow migration of the autologous bone mesenchymal stem cells from the bone marrow cavity to the joint. Introducing an aperture into bone underlying the joint may involve, for example, abrading, microfracturing or drilling the bone underlying the hyaline cartilage defect. The hyaline cartilage defect may include a full-thickness chondral defect. Applying the membrane to the joint may precede infiltrating the joint with autologous mesenchymal stem cells or alternatively, infiltrating the joint with autologous mesenchymal stem cells may precede applying the membrane to the joint. The method may further include securing the membrane to the joint, for example by attaching at least one fastener to the membrane and the joint. A fastener may be a biocompatible glue such as a fibrin glue, a suture, a tissue weld, a dart, a staple, a screw, or a tack. The method may further include applying to the joint a DBM composition, crushed bone and/or allogenic bone.

In another aspect the present disclosure provides a method for repairing a full-thickness chondral defect in a joint of a patient in need of such repair, the method comprising: microfracturing bone underlying the joint; applying to the joint a membrane comprising a tissue matrix comprising a high molecular weight caprolactone polymer entangled with a polysaccharide, wherein the membrane has a thickness of at least about 0.5 mm up to about 3 mm; and anchoring the membrane to the joint. The joint may be for example a knee joint.

DETAILED DESCRIPTION

The present disclosure describes a synthetic, flexible tissue matrix for supporting tissue repair, which is composed of certain high molecular weight polymers entangled with a polysaccharide, and optionally includes small molecule flexibility agents.

Surprisingly, the high molecular weight polymers, when entangled with a polysaccharide such as hyaluronic acid polymers through a dual solvent emulsion process, form matrices with the following beneficial aspects relative to a tissue matrix which inc0udes only polylactic acid (PLA) polymers, polyglycolic acid (PGA) polymers, or polymers consisting of a co-polymer of polylactic and polyglycolic acid (PLGA) entangled with hyaluronic acid polymers: 1)

increased flexibility at temperatures usually encountered in operating theater (e.g., 15 to 20° C.), while retaining the compressive resistant nature of the matrix; 2) increased aqueous absorption at physiological temperatures while maintaining a good dissolution profile relevant to the time scales for tissue regeneration; and 3) reductions in the appearance of a shiny surface on the strips of matrix, which in other matrices which incorporate only PLA, PGA or PLGA polymers result in migration of hyaluronic acid away from one surface during the manufacturing process.

The observed improved flexibility avoids or reduces the need to further treat or manipulate the tissue matrix in the surgical environment. In contrast, a tissue matrix using only PLA, PGA or PLGA polymers is relatively brittle under these surgical conditions, and thus requires some form of additional heating to facilitate its use. Without being bound by theory, it is believed that the increased absorbency of the improved tissue matrices described herein may be related to an improved ability for these matrices to imbibe and attach cellular component and further tissue formation.

The flexible tissue matrix can be used in methods for repairing a full-thickness chondral defect in a joint of a patient in need of treatment. Defects which may be treated may be any form of joint defect involving loss of or damage to hyaline cartilage, such as, but not limited to, a full-thickness defect, a partial-thickness defect, an age-related degenerative disease defect such as osteoarthritis, a congenital defect, or an injury resulting from trauma. In particular, such methods may include contacting the joint with, or introducing into the joint, cells which may differentiate into chondrocytes, such as mesenchymal stem cells, and applying to the joint a membrane comprising a flexible tissue matrix as described herein. Contact between the damaged joint and autologous mesenchymal stem cells from the underlying bone may be achieved for example using a microfracture technique as described in further detail below.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "mesenchymal stem cells" refers to pluripotent cells which originate within juvenile or adult mesenchymal tissue. Autologous mesenchymal stem cells may be autologous bone mesenchymal stem cells, i.e., autologous mesenchymal stem cells which originate within the marrow cavity of a bone.

As used interchangeably herein, the terms "demineralized bone matrix" and "DBM" refer to allograft bone tissue with the inorganic mineral removed, leaving organic collagen including biologically active bone morphogenetic proteins.

The terms "hyaluronic acid", "hyaluronate" and "HyA" are used interchangeably herein.

B. Flexible Tissue Matrix

The success of a bone graft is determined by its ability to recruit host cells to the site of the graft and modulate their conversion into bone-forming cells such as osteoblasts, to repair the defect. This will depend on the osteoconductive, osteoinductive and osteogenic capabilities of the graft. Currently, autograft bone harvested from the iliac crest is considered the 'gold standard' due to its superior osteogenic properties. However, associated donor site morbidity, an increased surgery and recovery time, and a limited supply of donor bone are limiting its use. Allograft bone is a logical alternative to autograft. However, it must be rigorously processed and terminally sterilized prior to implantation to remove the risk of disease transmission or an immunological response. This processing removes the osteogenic and osteoinductive properties of the graft, leaving only an osteoconductive scaffold.

DBM has superior biological properties to un-demineralized allograft bone, as the removal of the mineral increases the osteoinductivity of the graft. Currently, a range of DBM products are commercially available and approved by the Food and Drug Administration for clinical use.

Membranes comprising a tissue matrix comprising a polyester entangled with a polysaccharide, and methods of entangling a polyester and a polymer using a dual solvent emulsion process, are described in U.S. Pat. No. 8,192,759, "Tissue Matrix System," the entire disclosure of which is incorporated herein by reference. "Entanglement" and related terms, as used herein, refer to a state of polymers in melts or concentrated solutions above the overlap concentration, in which polymers interpenetrate one another and motion of the molecules is restricted to movement along a virtual tube which surrounds each molecule. (See, e.g., Glossary of Colloid and Polymer Science (available at world wide web studsvik.uu.se/pwwwp/Rennie/gloss.htm#E).

The present disclosure, however, provides an improved, flexible tissue matrix for supporting tissue repair, which is composed of certain high molecular weight polymers entangled with a polysaccharide and optionally further entangled with a polyester polymer. As used herein, the term "entangled" refers to the spatial relationship between a high molecular weight caprolactone polymer and a polysaccharide such as hyaluronic acid which is achieved using the dual solvent emulsion process described herein, and optionally further with respect to a polyester polymer optionally included in the flexible tissue matrix. The flexible tissue matrix optionally further includes small molecule flexibility agents. The flexible tissue matrix optionally further includes one or more growth factors, osteostimulative agents, and/or bone morphogenetic proteins, which may be obtained by prior isolation from allogenic bone. Additionally, in use, the flexible tissue matrix may be combined with any such growth factors, osteostimulative agents, and/or bone morphogenetic proteins, or with other materials such as allogenic bone, crushed cancellous bone, crushed cortical bone, or a DBM composition.

For the flexible tissue matrix, a high molecular weight polymer may be a caprolactone polymer such as polycaprolactone (PCL); a co-polymer of polylactic acid (PLA) and polycaprolactone (poly(lactide-co-caprolactone) (PLCL); a co-polymer of polyglycolic acid (PGA) and polycaprolactone (poly(glycolide-co-caprolactone) (PGCL); a co-polymer of polycaprolactone and both polylactic acid and polyglycolic acid (e.g., PGA-PLCL, PLA-PGCL); a co-polymer of polyethylene glycol (PEG), polylactic acid and polycaprolactone (e.g., PEG-PLCL, PLA-PEG-PCL and PLA-PEG-PLCL); a co-polymer of polyethylene glycol, polyglycolic acid and polycaprolactone (e.g., PEG-PGCL, PGA-PEG-PCL and PGA-PEG-PGCL); or a co-polymer of polyethylene glycol, polylactic acid, polyglycolic acid and polycaprolactone (e.g., PLA-PEG-PGCL, PGA-PEG-PLCL, PLA-PEG-PGA-PCL; PGA-PEG-PLA-PCL). Any of these high molecular weight polymers may further be combined in a polymer blend with a second polymer selected from polylactic acid (PLA), polyglycolic acid (PGA), or a co-polymer of polylactic acid and polyglycolic acid (PLGA). The polymers in the matrix do not, however, consist solely of PLA, PGA or PLGA, although any of these polymers can be used in combination with any of the high molecular weight caprolactone polymers.

The polysaccharide may be hyaluronic acid, chondroitin sulfate, dermatan sulfate, keratan sulfate, heparan, heparan sulfate, dextran, dextran sulfate, alginate, or any combination thereof, including any of these existing as multiple polymers, for example in solution. In non-limiting example, a tissue matrix comprises a high molecular caprolactone weight polymer such as, but not limited to, a co-polymer of polylactic acid and polycaprolactone (poly(lactide-co-caprolactone), and hyaluronic acid polymers. For example, both types of polymers (high molecular caprolactone weight polymers and hyaluronic acid polymers) are entangled with another via the dual solvent emulsion process described herein. As used herein, the term "hyaluronic acid" may refer to the free acid form of hyaluronic acid, a salt of hyaluronic acid such as sodium hyaluronate, or a combination thereof. Hyaluronic acid polymers may be obtained from a commercial source, such as a hyaluronic acid distributed by Lifecore Biomedical, Inc, Chaska, MN, and having an average molecular weight of from about 100,000 to about 2,000,000 Daltons. In non-limiting example, the hyaluronic acid may be sodium hyaluronate having an average molecular weight of about 1,700,000.

Surprisingly, high molecular weight caprolactone polymers may be successfully entangled with polysaccharide polymers such as hyaluronic acid polymers using a dual solvent emulsion process, and moreover, the resulting matrix exhibits the following unexpected, beneficial aspects relative to a tissue matrix which is composed solely of PLA, PGA or PLGA entangled with hyaluronic acid polymers: 1) increased flexibility at temperatures usually encountered in the operating theater (e.g., 15 to 20° C.), while retaining the compressive resistant nature of the matrix; 2) increased aqueous absorption at physiological temperatures while maintaining a good dissolution profile relevant to the time scales for tissue regeneration; and 3) reductions in the appearance of a shiny surface on the strips of matrix, which in other polymer matrices which incorporate only PLA, PGA or PLGA results in migration of hyaluronic acid away from one surface during the manufacturing process.

The observed characteristics of the resulting synthetic tissue matrix, including in particular the improved flexibility thereof, avoids or reduces the need to further treat or manipulate the tissue matrix in a surgical environment. In contrast, a tissue matrix using only PLA, PGA or PLGA is comparatively brittle under surgical conditions, and thus requires some form of additional treatment as heating to facilitate its use. Without being bound by theory, it is believed that the increased absorbency of the improved synthetic tissue matrices described herein may be related to an improved ability for these matrices to imbibe and attach cellular component and further tissue formation.

Once implanted in vivo, the flexible tissue matrix serves as scaffold that provides a microenvironment that is both biocompatible with and conducive to new bone formation. The high molecular weight polymer and optional additional polyester polymer provide(s) a three-dimensional structure, and a reliable resorption rate at the site of implantation which is consistent with the rate of endochondral bone remodeling. Additionally, hyaluronic acid is believed to play an important role in tissue regeneration and repair, and to assist important early events in bone formation by promoting the migration, proliferation, and differentiation of osteogenic cells. A combination of a high molecular weight caprolactone polymer with a polysaccharide such as hyaluronic acid, and optionally further with a polyester polymer such as PLA, PGA or PLGA, when entangled according to the process described herein, provides a scaffold with improved cohesiveness, molding properties and handling characteristics relative to other known synthetic scaffolds and matrices.

A tissue matrix is prepared using a dual solvent emulsion process as described herein below and in the Examples. Briefly, a high molecular weight caprolactone polymer as described hereinabove is dissolved in an organic solvent such as ethyl acetate, a halogenated solvent such as methylene dichloride, chloroform, or tetrahydrofuran, or any combination thereof as known to those of routine skill in the art. Once the high molecular weight caprolactone polymer is dissolved, optionally a polyester polymer such as PLA, PGA or PLGA may be added to the solution and also dissolved. When a high molecular weight polycaprolactone polymer is combined with another (second) polymer such as PGA, PLA or PLGA, they may be combined in a volume ratio of about 10:1 to about 1:1 (second polymer:high molecular weight polycaprolactone polymer). For example, PLGA may be combined with PLCL at a volume ratio of about 10:1 to about 1:1 (PLGA:PLCL). A polysaccharide such as, but not limited to hyaluronate (HyA) is dissolved in water. The two solutions (total polymer including high molecular weight polycaprolactone in organic solvent, and polysaccharide in water) are combined at a volume ratio of at least about 1.5:1 (3:2), about 2:1, about 3:1, or any volume ratio from about 4:1 to about 15:1 (total polymer including high molecular weight polycaprolactone in organic solvent:polysaccharide in water) and mixed using any agitation method as known in the art to form an emulsified mixture, or emulsion. For example, a homogenizer as known in the art can be used for agitation. The emulsion is then frozen. After freezing, the frozen emulsion is lyophilized to remove the two solvents, thereby yielding a matrix comprising the high molecular weight caprolactone polymer, and optionally a polyester polymer such as PLA, PGA or PLGA entangled with the polysaccharide. As described in further detail herein below, prior to freezing, a certain volume of the emulsion can be poured into a flat mould of predetermined volume such that the certain volume of emulsion results in a layer of emulsion of a desired thickness. After freezing and lyophilizing, the resulting matrix is formed as a thin film or membrane of the desired thickness, which is then removed from the mould for use in repairing tissue, or for further processing to achieve a desired membrane thickness, for example using rollers.

A tissue matrix optionally further includes one or more flexibility agents to promote or further enhance the flexibility of the tissue matrix. One or more flexibility agents may be selected from triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate, or any combination thereof. Alternatively, one or more flexibility agents may be selected from polyethylene glycol, polyethylene glycol monoalkyl ether, propylene glycol, glycerin, triacetin or any combination thereof. The flexibility agent may be added to either the total polymer including high molecular weight polycaprolactone in organic solvent, or to the aqueous polysaccharide solution, depending on the solubility characteristics of the flexibility agent as will be readily known or determined by one of routine skill in the art.

A flexible tissue matrix as described herein may further comprise one or more growth factors, osteostimulative agents, and/or bone morphogenetic proteins (BMPs), which may be synthetic, for example obtained by prior synthesis or by recombinant protein production as known in the art, or by isolation from a natural source such as allogenic bone. For example, and without being limited by theory, certain growth factors are believed to promote formation of hyaline cartilage by promoting differentiation of mesenchymal stem cells into hyaline cartilage-forming chondrocytes, thereby speeding the healing process. Non-limiting examples of such growth factors which may be incorporated into a membrane of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue, including allogenic bone tissue. For example, one or more growth factors such as one or more BMPs may be isolated from allogenic bone and incorporated in the flexible tissue matrix. A flexible tissue matrix as described herein may comprise, in addition to or instead of a growth factor, a collagen such as type I collagen, type II collagen, type IX collagen, type X collagen, or type XI collagen. A growth factor or a collagen may be incorporated in the matrix by first preparing an aqueous solution or suspension of the growth factor or collagen (e.g., a collagen suspension), and adding the solution or suspension to the combination of the total polymer in organic solvent and the polysaccharide in water, before or during the emulsification process.

Additionally, in use the flexible tissue matrix may be combined with any such growth factors, osteostimulative agents, and/or bone morphogenetic proteins, and/or with other materials such as allogenic bone, crushed cancellous bone, crushed cortical bone, or a DBM composition.

A flexible tissue matrix as described herein may be formed as a membrane for convenient implantation at the site of a defect. For example, a flexible tissue matrix may be formed as a membrane having a thickness of at least about 0.5 mm up to about 3 mm. A membrane may be formed using methods known to those of routine skill in the art for preparing thin films from liquid or fluid materials. For example, a membrane may be formed by preparing the dual solvent emulsion as described elsewhere herein, pouring a certain volume of the emulsion into a mould of predetermined size, and then lyophilizing the emulsion in the mould. Thickness of the membrane can be further controlled by regulating the rate of pour into the mould and stopping the pour when a layer of emulsion of desired thickness within the mould is obtained. After the lyophilized emulsion has been removed from the mould, the thickness of the resulting membrane can still further be modified by rolling the material through rollers to obtain a membrane of the desired thickness. Alternatively, a membrane may be formed using an extrusion process in which the emulsion is extruded at a predetermined thickness.

C. Methods

The present teachings encompass methods for repairing a full-thickness chondral defect in a joint of a patient in need of treatment. The present methods of joint repair may be applied to any body joint comprising hyaline cartilage, such as, but not limited to, a joint of a knee, an elbow, an ankle, a shoulder, a jaw or a wrist. A joint may be any joint comprising articular cartilage, such as a joint of a long bone, for example a knee joint comprising articular cartilage of a femur. Furthermore, the methods may be used with both humans and animals having joint defects, including, without limitation, a mammal such as a companion animal or farm animal (e.g., a cat, a dog, a sheep, a cow, a goat, a pig, or a horse). Defects which may be treated may be any form of joint defect involving loss of or damage to hyaline cartilage, such as, but not limited to, a full-thickness defect, a partial-thickness defect, an age-related degenerative disease defect such as osteoarthritis, a congenital defect, or an injury resulting from trauma.

Treatment of a joint defect using the methods disclosed herein is believed to promote deposition of hyaline cartilage in the defect rather than fibrocartilage. Briefly, the methods comprise contacting the joint with, or introducing into the joint, cells which may differentiate into chondrocytes, such as mesenchymal stem cells, and applying to the joint a membrane comprising a flexible tissue matrix as described herein. Such methods using a tissue matrix comprising only a polyester polymer and hyaluronate are described for example in U.S. 2007-0128155 A1 (U.S. Pat. App. Ser. No. 11/635,265), the entire disclosure of which is herein incorporated by reference. Most conveniently, such mesenchymal stem cells may be autologous mesenchymal stem cells originating in the bone underlying the damaged joint, although mesenchymal stem cells from other bones may be used as well. Contact between the damaged joint and autologous mesenchymal stem cells from the underlying bone may be achieved most readily by a microfracture technique, i.e., by introducing one or more apertures into the subchondral bone underlying the defective joint. Such apertures need be at least large enough to allow passage of the mesenchymal stem cells from the bone mesenchyme to the joint. Several well-established procedures may be used to form such passages, such as, without limitation, abrasion (such as abrasion arthroplasty), perforation (e.g., with a surgical awl), and drilling of the bone. These and other treatment procedures are well known to skilled artisans, and described in detail in the literature, for example in references such as Steadman, J.R. et al., Clinical Orthopaedics and Related Research 391S: S362-S369, 2001; and Steadman et al., J. Knee Surg. 15(3):170-176 (2002).

Without being limited by theory, it is believed that following introduction of passages or perforations into the bone, mesenchymal stem cells may migrate out from the bone marrow cavity through the passages, and populate the joint. Exposure of the mesenchymal stem cells to the local environment of the joint leads to differentiation of the stem cells into cartilage-forming chondrocytes. In the further presence of a membrane comprising a tissue matrix as described herein, the chondrocytes produce hyaline cartilage rather than fibrocartilage. The introduction of the cells under these conditions may thereby restore the cartilage of a defective joint to a state more closely resembling that of the joint pre-injury.

Accordingly, the methods of the present disclosure may include microfracturing bone underlying the joint, and applying to the joint a membrane comprising a flexible tissue matrix as described herein. Microfracturing may precede the application to the joint of a membrane comprising a flexible tissue matrix, or vice versa. Additionally, the membrane can be manually shaped according to the contours of a joint. The method may further comprise securing the membrane to the joint, for example anchoring or fastening the membrane to the joint, or immobilizing the membrane at the joint. Securing the membrane may be part of the surgical intervention in the treatment of a patient. Accordingly, in various aspects, a skilled artisan such as an orthopaedic surgeon may secure a membrane at the site of defect in a patient, using at least one fastener, to thereby retain the membrane at the site. Such retention of the membrane may promote the formation of hyaline cartilage by chondrocytes differentiated from mesenchymal stem cells. Examples of a fastener that may be used in the present methods include, without limitation, a biocompatible glue, a suture, a tissue weld, a dart, a staple, a screw, a tack, and a combination thereof. A biocompatible glue may be a fibrin glue, such as a fibrin sealant. A non-limiting example of a biocompatible glue that may be used with the present teachings is a fibrin sealant manufactured by Oesterreichisches Institut Fuer Haemoderivate G.M.B.H. in Vienna, Austria and distributed by Baxter Healthcare Corporation, Glendale, Calif., under the brand name TISSEEL® VH. Non-limiting examples of other fasteners which may be used instead of, or in addition to a biocompatible glue include sutures, tissue welds such as described in Helmsworth, T. F., et al., Laser Surgery Medicine 10: 576-583, 1990, staples, darts, pins and tacks. In some aspects, a fastener may comprise a biocompatible or bioabsorbable material such as, without limitation, a PLA/PLG polymer, or a non-absorbable material such as a biocompatible metal. A fastener may be an absorbable suture which passes through both the membrane and a joint, and thereby secures apposition of the membrane to the joint. Furthermore, in non-limiting example, the attaching may comprise gluing the membrane to the joint.

As indicated in the foregoing, introduction of at least one aperture in the subchondral bone may precede application of a membrane to the joint, or application of a membrane to the joint may precede the introduction of at least one aperture.

The present disclosure thus encompasses methods for repair of a full thickness chondral defect in a joint of a patient in need of treatment, the methods involving: a) introducing at least one aperture through bone underlying the joint, wherein the at least one aperture allows migration of mesenchymal stem cells from a marrow cavity of the bone to the joint, and b) applying to the joint a membrane comprising a flexible tissue matrix as described herein. The methods may further comprise securing the membrane to the joint, using attachment methods and devices as described herein and as otherwise well known to skilled artisans.

Additionally, in use the flexible tissue matrix may be combined with one or more growth factors, osteostimulative agents, and/or bone morphogenetic proteins, and/or with other materials such as allogenic bone, crushed cancellous bone, crushed cortical bone, or a DBM composition. For example, any of the joint treatment or repair methods optionally further comprises applying to the joint, or implanting at a joint defect site, one or more growth factors, osteostimulative agents, and/or bone morphogenetic proteins, and/or other material such as allogenic bone, crushed cancellous bone, crushed cortical bone, or a composition composed of DBM. For example, a DBM gel, putty or paste, or thin sheets or membranes of DBM, may be implanted at the joint defect site and/or placed in direct contact with the joint at the defect site. Several suitable DBM substances are commercially available for use in orthopedic surgeries, such as but not limited to Osteofil® IC allograft paste (RTI Biologics Inc., Alachua, Fla.), Grafton® DBM products including putty, paste, gel and sheets (strips) (Medtronics Biologics, Inc., Memphis Tenn.), Dynagraft D™ (Citagenix, Inc., Laval, Qc, Canada), and demineralized trabecular bone products such as but not limited to MatrixOI™(Cellright, Inc., Universal City, Tex.). Sheets or strips comprising or made of any of the foregoing materials may, for example, have approximately the same thickness as a membrane comprising the flexible tissue matrix, e.g., at least about 0.5 mm up to about 3 mm. Any of the foregoing materials in any of their various forms may be used generally according to the manufacturer's instructions and in combination with the flexible tissue matrix as may be determined according to guidelines well known to those of routine skill in the art. Application to the joint, or implantation at the joint defect site, of one or more growth factors, osteostimulative agents, and/or bone morphogenetic proteins, and/or with other materials such as allogenic bone, crushed cancellous bone, crushed cortical bone, or a DBM composition, or a composition comprising any one or more such elements, may take place at any point relative to application of the flexible membrane to the joint, and introduction of at least one aperture for microfracturing.

The following examples are illustrative, and are not intended to limit the scope of the claims.

EXAMPLES

Example 1: Entanglement of a Polyester, poly(lactide-co-glycolide) (PLGA) and a Polysaccharide (Hyaluronic Acid)

This example illustrates a method of constructing an entangled matrix comprising a polyester and a polysaccharide. In this example, poly(lactide-co-glycolide) having molecular weight of $1.5 \times 10^5$ is dissolved in dichloromethane (125 mg/ml) and with Hyaluronate (HyA) of molecular weight of about $1.3 \times 10^6$ Dalton is dissolved in water (15 mg/ml). The two polymer solutions, 2 parts PLGA, and 1 part HyA, are mixed with 1 part Milli Q water by vortexing at high speed for about 5 minutes. The emulsified mixture is immediately poured into a mould pre-cooled at $-70°$ C. in a bath containing dry ice in isopropyl alcohol. After freezing, the mold and its contents are transferred into a second container that is loaded with dry ice and connected to vacuum line. Organic solvent is removed by this process at the temperature between $-70°$ C. to $-40°$ C., leaving HyA in wet-ice phase. Water is then removed by raising the temperature to $-10°$ C. under vacuum.

Example 2: Entanglement of the High Molecular Weight Caprolactone Polymer poly(lactide-co-caprolactone (PLCL), and PLGA, and a polysaccharide (hyaluronic acid)

In this example, poly(lactide-co-caprolactone) (PLCL) having a molecular weight of about $2 \times 10^5$ is dissolved in ethyl acetate (80 mg/ml) containing polyethylene glycol 400 (PEG400) (20 mg/ml). Once the PLCL is dissolved, poly(lactide-co-glycolide) (PLGA) having a molecular weight of about $1.5 \times 10^5$ is added (240 mg/ml) and dissolved. Hyaluronate (HyA) of molecular weight of about $1.5 \times 10^6$ is dissolved in water (20 mg/ml). The two polymer solutions, 3 parts PLGA/PLCL, and 2 parts HyA, are mixed, poured in moulds sized sufficiently to produce a membrane having a thickness of 3 mm, and frozen as described in Example 1. After freezing, the frozen emulsion is lyophilized to remove the two solvents, yielding a membrane formed of a flexible tissue matrix comprising PLGA/PLCL entangled with HyA.

Example 3: Treatment of a Knee Injury

In this example, an athletic patient presents with a traumatic knee injury to an orthopedic surgeon. A diagnosis is made of damaged articular cartilage of the femoral condyle. The surgeon performs a microfracture procedure on the patient's femoral condyle, creating channels through the bone underlying the hyaline cartilage using an awl or drill. The surgeon selects a membrane having a thickness of 3 mm formed from a tissue matrix prepared as described in Example 2, and shaped to follow the contours of the condyle. The surgeon coats one side of the membrane with TISSEEL® VH fibrin sealant and then applies the membrane to the damaged femoral condyle using gentle pressure. The patient is instructed to keep pressure off the knee for a period of weeks. The condyle is repaired with new hyaline cartilage by six months after the surgical intervention.

Example 4: Treatment of a Knee Injury Also Using a DBM Composition

Treatment of a knee injury is carried out substantially as described in Example 3 above. A membrane formed of DBM and having a thickness of no more than 3 mm is also applied to the damaged femoral condyle and secured in position using TISSEEL® VH fibrin sealant.

Example 5: Treatment of Osteoarthritis

In this example, a patient with osteoarthritis presents with a full-thickness chondral defect in an elbow joint. A surgeon performs a microfracture procedure on the humerus underlying the joint using a drill or awl. A membrane having a thickness of 1 mm and formed from a tissue matrix prepared substantially as described in Example 2, and shaped to follow the contours of the condyle, is positioned by the surgeon upon the condyle. The surgeon secures the membrane in place with a series of screws made of a resorbable PLA/PLG polymer. Following surgery, new hyaline cartilage deposits along the condyle over a six month period. The new cartilage is anatomically indistinguishable from normal hyaline cartilage.

Example 6: Treatment of the Shoulder

In this example, a middle age male presents with a traumatic dislocation of the shoulder. A diagnosis is made of disruption of the articular cartilage covering the head of the humerus at its articulation with the glenoid socket of the scapula. The patient is operated upon by a surgeon, who performs a microfracture procedure on the head of the humerus. A membrane having a thickness of 1 mm and formed from a tissue matrix prepared as described in Example 2, and shaped to approximate the contours of the humeral head, is positioned by the surgeon upon the humeral head. The surgeon secures the membrane in place with a series of resorbable pins. Following surgery, new hyaline cartilage deposits along the condyle over a period of six months. The new cartilage is anatomically indistinguishable from normal hyaline cartilage.

One skilled in the art would readily appreciate that the articles and kits described in the present disclosure are well adapted to carry out the objects and obtain the ends and advantages mentioned, as well as those inherent therein. The methods, procedures, treatments and kits described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference. Any discussion of references cited herein is intended merely to summarize the assertions made by their authors and no admission is made that any reference or portion thereof constitutes relevant prior art.

Applicant reserves the right to challenge the accuracy and pertinency of the cited references.

REFERENCES

Rodrigo J.I., et al., Osteoarticular injuries of the knee. pp. 2077-2082, In: Chapman, M.W. (ed): OPERATIVE ORTHOPAEDICS, Vol. 3, 2nd Ed. Lippincott, Philadelphia, Pa., 1993

Tippet J.W., Articular cartilage drilling and osteotomy in osteoarthritis of the knee, pp. 325-339, in: McGinty, J.B. (ed): Operative Arthroscopy. Raven Press, New York, N.Y., 1991

Vangsness, C.T., et al., Amer. 1 Orthop. 33 (2 Suppl): 29-34, 2004; Textbook of Arthroscopy, Miller, M.D. et al., ed. Saunders, 2004

The Adult Knee, Callaghan, J. 1. et al., ed., Lippincott Williams & Wilkins, 2003;

Operative Treatment of Elbow Injuries, Baker, C.L., et al., ed., Springer, 2002

Osteoarthritis: Fundamentals and Strategies for Joint-preserving Treatment, Grifka, J.J., et al., ed., Springer, 2000

Reconstructive Surgery of the Joints, Morrey, B.F., et al., ed., Churchill Livingstone, 1996

Operative Arthroscopy, McGinty, J.B., et al., ed., Lippincott-Raven, 1996

The Knee, Scott, W.N., ed., Mosby-Year Book, 1994

Surgical Repair and Reconstruction in Rheumatoid Disease, Benjamin, A., et al., Spring-Verlag, 1993

The Knee: Form, Function, Pathology, and Treatment; Larson, R.L., et al., ed., W.B. Saunders, 1993

O'Connor's Textbook of Arthroscopic Surgery, Shahriaree, H., ed., 1B. Lippincott, 1992.

What is claimed is:

1. A method for repairing a hyaline cartilage defect in a joint in a mammal, the method comprising: infiltrating the joint with autologous mesenchymal stem cells; and applying to the joint a membrane comprising a tissue matrix comprising total polymers comprising a caprolactone polymer and at least one additional polyester polymer other than a caprolactone polymer which is not copolymerized with the caprolactone polymer, wherein the total polymers are entangled with a polysaccharide following combination of the total polymers and the polysaccharide in a dual solvent emulsion, said dual solvent emulsion being formed by the steps of:
  i. dissolving the total polymers in an organic solvent;
  ii. dissolving the polysaccharide in an aqueous solvent;
  iii. blending the total polymers in the organic solvent with the polysaccharide in an aqueous solvent to form the dual solvent emulsion; and
  iv. removing the organic solvent and aqueous solvent from the emulsion to form a flexible matrix comprising the total polymer molecules entangled with polysaccharide polymer molecules; wherein the weight ratio of the polyester polymer to the caprolactone polymer ranges from about 1:1 to about 4:1.

2. A method according to claim 1, wherein infiltrating the joint with autologous mesenchymal stem cells comprises introducing at least one aperture into bone underlying the joint, wherein the at least one aperture is sufficiently large to allow migration of autologous bone mesenchymal stem cells from the bone marrow cavity to the joint.

3. A method according to claim 1, wherein the hyaline cartilage defect comprises a full-thickness chondral defect.

4. A method according to claim 1, wherein the membrane has a thickness of about 0.5 mm up to about 3 mm.

5. A method according to claim 1, wherein the tissue matrix comprises a caprolactone polymer selected from polycaprolactone, a co-polymer of polylactic acid and polycaprolactone, a co-polymer of polyglycolic acid and caprolactone, a co-polymer of polylactic acid, polyglycolic acid polycaprolactone; a co-polymer of polyethylene glycol, polylactic acid and polycaprolactone; a co-polymer of polyethylene glycol, polyglycolic acid and polycaprolactone; and a co-polymer of polyethylene glycol, polylactic acid, polyglycolic acid, and polycaprolactone.

6. A method according to claim 5, wherein the tissue matrix comprises a co-polymer selected from a co-polymer of polylactic acid and polycaprolactone, a co-polymer of polyglycolic acid and caprolactone, a co-polymer of polylactic acid and polyglycolic acid; a co-polymer of polyethylene glycol, polylactic acid and polycaprolactone; a co-polymer of polyethylene glycol, polyglycolic acid and polycaprolactone; and a co-polymer of polyethylene glycol, polylactic acid, polyglycolic acid, and polycaprolactone.

7. A method according to claim 1, wherein the tissue matrix further comprises at least one flexibility agent at a weight ratio of caprolactone polymer to flexibility agent in the tissue matrix is 9:1 to 99:1.

8. A method according to claim 7, wherein the flexibility agent is selected from the group consisting of triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate, and any combination thereof.

9. A method according to claim 7, wherein the flexibility agent is selected from the group consisting of polyethylene glycol, polyethylene glycol monoalkyl ether, propylene glycol, glycerin, triacetin and any combination thereof.

10. A method according to claim 6, wherein the tissue matrix comprises a co-polymer of polylactic acid and polycaprolactone, wherein the weight ratio of polylactic acid to polycaprolactone is about 95:5 to 1:9.

11. A method according to claim 6, wherein the tissue matrix comprises a co-polymer of polylactic acid and polycaprolactone, wherein the weight ratio of polylactic acid to polycaprolactone is about 7:3.

12. A method according to claim 6, wherein the at least one additional polyester polymer other than a caprolactone polymer is selected from polylactic acid, polyglycolic acid, and a copolymer of polylactic acid and polyglycolic acid.

13. A method according to claim 12, wherein the tissue matrix comprises polylactic acid and a co-polymer of polyglycolic acid and polycaprolactone.

14. A method according to claim 1, wherein the polysaccharide comprises hyaluronic acid polymers.

15. A method according to claim 14, wherein the hyaluronic acid polymers are oxidized or covalently cross linked.

16. A method according to claim 14, wherein the caprolactone polymer and the hyaluronic acid polymers are present in a weight ratio of from 99:1 to 1:99.

17. A method according to claim 1, wherein the tissue matrix further comprises at least one growth factor selected from the group consisting of basic fibroblast growth factor (bFGF), transforming growth factor (TGF-β), BMP-2, ADMP-1, a hedgehog protein, an insulin-like growth factor, a platelet-derived growth factor, an interleukin, a colony-stimulating factor, and an activin.

18. A method according to claim 1, wherein the tissue matrix further comprises a bone morphogenetic protein, a type I collagen, or a type II collagen.

19. A method according to claim 1, further comprising anchoring the membrane to the joint, wherein anchoring the membrane to the joint comprises applying to the joint at least one fastener which secures the membrane to the joint, wherein the at least one fastener is selected from the group consisting of a biocompatible glue, a suture, a tissue weld, a dart, a staple, a screw, and a tack.

20. A method according to claim 19, wherein the biocompatible glue is a fibrin glue.

21. A method according to claim 1, further comprising applying to the joint a demineralized bone matrix (DBM) composition, crushed bone, or allogenic bone.

22. A method for repairing a full-thickness chondral defect in a joint of a patient in need of such repair, the method comprising:
  a) microfracturing bone underlying the joint;
  b) applying to the joint a membrane comprising a tissue matrix comprising total polymers comprising a caprolactone polymer and at least one additional polyester polymer other than a caprolactone polymer which is not copolymerized with the caprolactone polymer, wherein the total polymers are entangled with a polysaccharide following combination of the total polymers and the polysaccharide in a dual solvent emulsion, wherein the membrane has a thickness of at least about 0.5 mm up to about 3 mm; and anchoring the membrane to the joint, said membrane being formed by the steps of:
    i. dissolving the total polymers in an organic solvent;
    ii. dissolving the polysaccharide in an aqueous solvent;
    iii. blending the total polymers in the organic solvent with the polysaccharide in an aqueous solvent to form a dual solvent emulsion; and
    iv. removing the organic solvent and aqueous solvent from the emulsion to form a flexible matrix comprising the caprolactone polymer molecules entangled with polysaccharide polymer molecules; wherein the weight ratio of the polyester polymer to the caprolactone polymer ranges from about 1:1 to about 4:1.

23. A method according to claim 22, wherein the joint is a knee joint.

24. A method according to claim 22, wherein anchoring the membrane to the joint comprises applying to the joint at least one fastener which secures the membrane to the joint, wherein the at least one fastener is selected from the group consisting of a biocompatible glue, a suture, a tissue weld, a dart, a staple, a screw, and a tack.

25. A method according to claim 22, wherein the caprolactone polymer is selected from polycaprolactone; a co-polymer of polylactic acid and polycaprolactone; a co-polymer of polyglycolic acid and polycaprolactone; a co-polymer of polylactic acid, polyglycolic acid and polycaprolactone; a co-polymer of polyethylene glycol, polylactic acid and polycaprolactone; a co-polymer of polyethylene glycol, polyglycolic acid and polycaprolactone; and a co-polymer of polyethylene glycol, polylactic acid, polyglycolic acid and polycaprolactone.

26. A method according to claim 25, wherein the tissue matrix comprises a co-polymer selected from a co-polymer of polylactic acid and polycaprolactone; a co-polymer of polyglycolic acid and polycaprolactone; a co-polymer of polylactic acid and polyglycolic acid; a co-polymer of polyethylene glycol, polylactic acid and polycaprolactone; a co-polymer of polyethylene glycol, polyglycolic acid and polycaprolactone; and a co-polymer of polyethylene glycol, polylactic acid, polyglycolic acid, and polycaprolactone.

27. A method according to claim 22, wherein the tissue matrix further comprises at least one flexibility agent.

28. A method according to claim 27, wherein the weight ratio of caprolactone polymer to flexibility agent in the tissue matrix is 9:1 to 99:1.

29. A method according to claim 28, wherein the flexibility agent is selected from the group consisting of triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate, and any combination thereof.

30. A method according to claim 28, wherein the flexibility agent is selected from the group consisting of polyethylene glycol, polyethylene glycol monoalkyl ether, propylene glycol, glycerin, triacetin, and any combination thereof.

* * * * *